United States Patent [19]

Virag

[11] 4,198,969
[45] Apr. 22, 1980

[54] SUCTION-OPERATED NEBULIZER

[75] Inventor: Robert A. Virag, Cary, Ill.

[73] Assignee: Baxter Travenol Laboratories, Inc., Deerfield, Ill.

[21] Appl. No.: 940

[22] Filed: Jan. 4, 1979

Related U.S. Application Data

[63] Continuation-in-part of Ser. No. 949,291, Oct. 6, 1978, abandoned.

[51] Int. Cl.² ............................................. A61M 11/02
[52] U.S. Cl. ................................ 128/200.21; 239/338;
239/309; 261/DIG. 65; 261/72 R; 222/630
[58] Field of Search ............ 128/194, 193, 188, 145.8,
128/145.6, 209, 210, DIG. 2, 173 R; 239/338,
309; 261/DIG. 65, 72 R; 222/630, 81, 82

[56] References Cited

U.S. PATENT DOCUMENTS

| | | | |
|---|---|---|---|
| 2,807,504 | 9/1957 | Bloxsom | 239/338 |
| 3,807,713 | 4/1974 | Cornett et al. | 261/222 |
| 3,826,255 | 7/1974 | Havstad et al. | 128/194 |
| 3,857,909 | 12/1974 | Huggins | 128/194 X |
| 3,915,386 | 10/1975 | Vora | 239/338 |
| 4,150,071 | 4/1979 | Pecina | 128/194 X |

Primary Examiner—Henry J. Recla
Attorney, Agent, or Firm—Paul C. Flattery; John P. Kirby, Jr.; Garrettson Ellis

[57] ABSTRACT

A nebulizer for forming a liquid mist in a stream of gas. The nebulizing chamber carries a liquid suction conduit adapted to communicate with a supply of liquid below the nebulizing chamber. Accordingly, as suction is exerted on the nebulizing chamber, for example, by a patient breathing in, liquid is drawn upwardly into the nebulizing chamber through the suction conduit. When the liquid reaches a predetermined level it enters into the nebulizing apparatus of the device, with the result that nebulization only takes place at a predetermined minimum level of suction.

17 Claims, 10 Drawing Figures

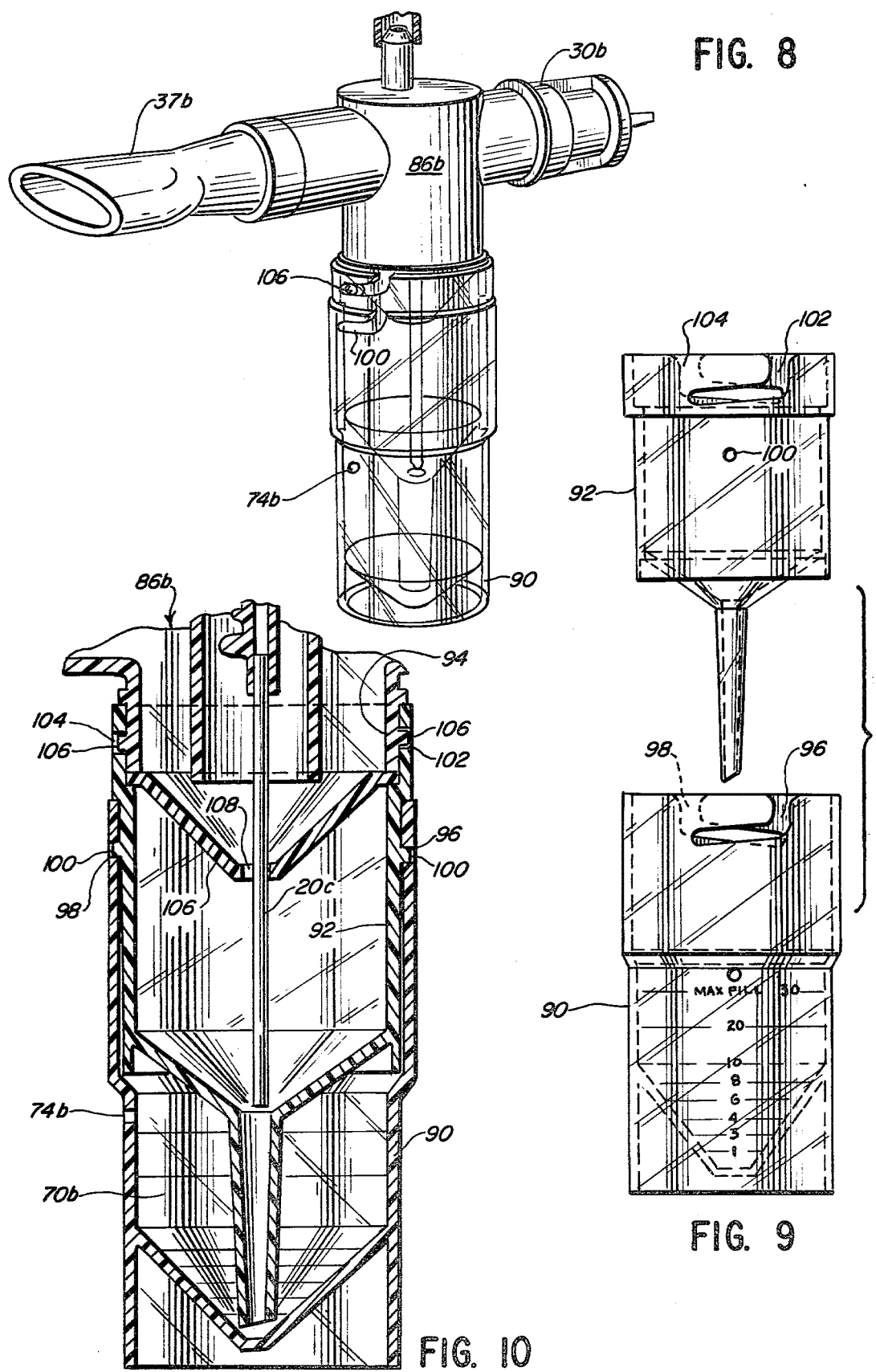

SUCTION-OPERATED NEBULIZER

CROSS-REFERENCE TO RELATED APPLICATION

This application is a continuation-in-part of U.S. Application Ser. No. 949,291, filed Oct. 6, 1978 now abandoned.

BACKGROUND OF THE INVENTION

Incentive spirometers are used in respiratory therapy to measure the breathing capacity or the sustained maximal inspiration of a patient. Typically, an incentive spirometer will include a light ball which can float in the air stream created by the breathing patient, to indicate the flow velocity, which, in turn, is a function of the vigor and depth of the patient's breathing.

Nebulizers are used in respiratory therapy to provide a liquid mist to a stream of gas, typically oxygen-air mixtures, which is conveyed to a patient. The mist that is added to the air stream may include water for the humidification of the oxygen supply to the patient, but also bronchodialators or mucolytic agents may be added and conveyed directly to the inner recesses of the lungs in mist form by the breathing of the patient.

Generally, nebulizing devices operate continuously, using an aspiration type device to suck up the liquid for nebulizing into a stream of oxygen gas, being forced through a nozzle by means of the well-known Bernoulli's principle. Accordingly, when the patient is not breathing, or is exhaling, the mist-laden oxygen tends to diffuse out of the device carrying the medicament with it.

In accordance with this invention, a nebulizing device is disclosed in which nebulization takes place only when a suction pressure is applied to the nebulizing chamber, for example, when a patient is breathing in. Furthermore, the device of this invention can be used as an incentive spirometer since the device may be adjusted so that the patient must breathe in with a certain minimum amount of vigor for nebulization to take place. Accordingly, the patient and a respiratory therapy technician can determine whether or not the patient is successfully meeting a specified breathing exercise goal by the use of the device of this invention, while simultaneously the same device can be used to provide nebulized gases to the patient.

Accordingly, since the device of this invention operates to nebulize liquids in the gas stream only on voluntary inspiration, the disadvantages of forced machine-controlled inspiration which are frequently, currently used are avoided. If natural, deep breathing becomes painful, the patient will stop inhaling, where a machine would continue to pressurize and possibly damage the lungs.

DESCRIPTION OF THE INVENTION

In accordance with this invention, a nebulizer for forming a liquid mist in a stream of gas comprises a nebulizing chamber, a gas inlet communicating with the nebulizing chamber, a liquid supply conduit within the nebulizing chamber, means for nebulizing liquid from the supply conduit into gas entering the nebulizing chamber through the gas inlet, and an outlet for nebulized gas communicating with the nebulizing chamber. The liquid supply conduit defines an open lower end within the nebulizing chamber below the nebulizing means.

In accordance with this invention, a liquid suction conduit extends from and communicates with the nebulizing chamber. The liquid suction conduit is adapted for communication with a source of liquid positioned below the nebulizing chamber.

As a result of this, the application of suction to the outlet, for example by the inspiration or inhalation of a patient, can cause liquid to be sucked through the liquid suction conduit into the nebulizing chamber. If the suction is sufficient, the nebulizing chamber can be filled to the depth of the open lower end of the liquid supply conduit. This permits nebulization to occur as the liquid supply conduit draws the liquid into the nebulizing means, for example by a conventional aspirator arrangement.

Upon the cessation of the suction through the outlet, the reduced pressure in the nebulizing chamber is eliminated, and the liquid accordingly runs out of the nebulizing chamber through the liquid suction conduit, to reduce the level of liquid therein. This exposes the open lower end of the liquid supply conduit and terminates nebulization, until the next surge of reduced pressure within the nebulizing chamber, caused, for example, by the next breath of the patient.

Preferably, the nebulizer of this invention utilizes an adjustable auxiliary air inlet which communicates with the nebulizing chamber having an aperture to the exterior of variable size. Accordingly, if the patient is very weak and has shallow breathing, the auxiliary air inlet may be shut off or opened to only a very small degree, so that only a light amount of suction by the breathing patient is required to suck up enough liquid through the liquid suction conduit to initiate aspiration.

With respect to a convalescing patient who should be forcing himself to breathe more deeply, the auxiliary air port may be opened wider, which forces the patient to breathe in more vigorously in order to obtain sufficient reduced pressure within the nebulization chamber to initiate nebulization with his breath. As a result of this, a respiratory technician can adjust the auxiliary air inlet as indicated by the specific situation, to provide a preselected, minimum inhalation flow rate on the part of the patient at which nebulization takes place, to match the breathing capability of the patient.

The liquid suction conduit may constitute a spike extending from the bottom of the nebulization chamber and carrying several longitudinal fins at the end of the spike, proximal to the nebulization chamber. Accordingly, the spike may penetrate an ampule of the desired liquid for nebulization, with fins passing through the access site of the ampule as well, to provide vent passages between the interior and exterior of the ampule.

In the drawings,

FIG. 8 is a perspective view of another embodiment of the nebulizer of this invention.

FIG. 9 is an exploded elevational view of the bottom portion of the nebulizer of FIG. 8.

FIG. 10 is a fragmentary elevational view of the bottom portion of the nebulizer of this invention.

Figure 1:
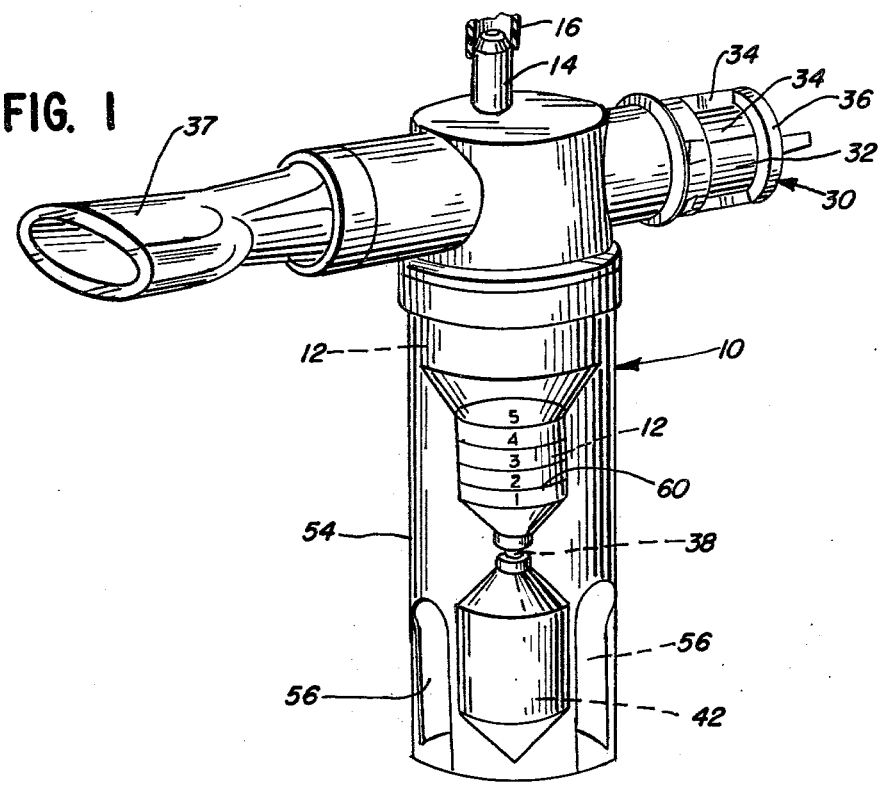
FIG. 1 is a perspective view of the suction operated nebulizer of this invention.
Figure 2:
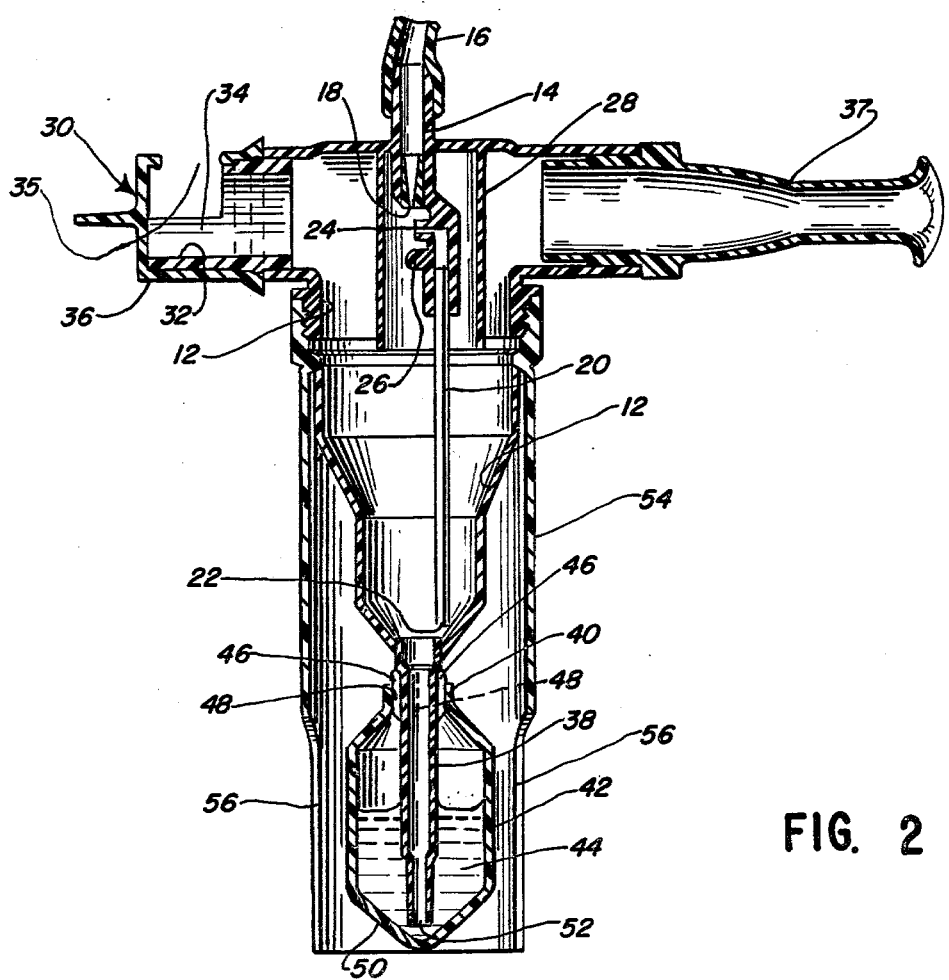
FIG. 2 is a vertical sectional view of the nebulizer of FIG. 1, showing the nebulizer under normal, ambient pressure conditions.
Figure 3:
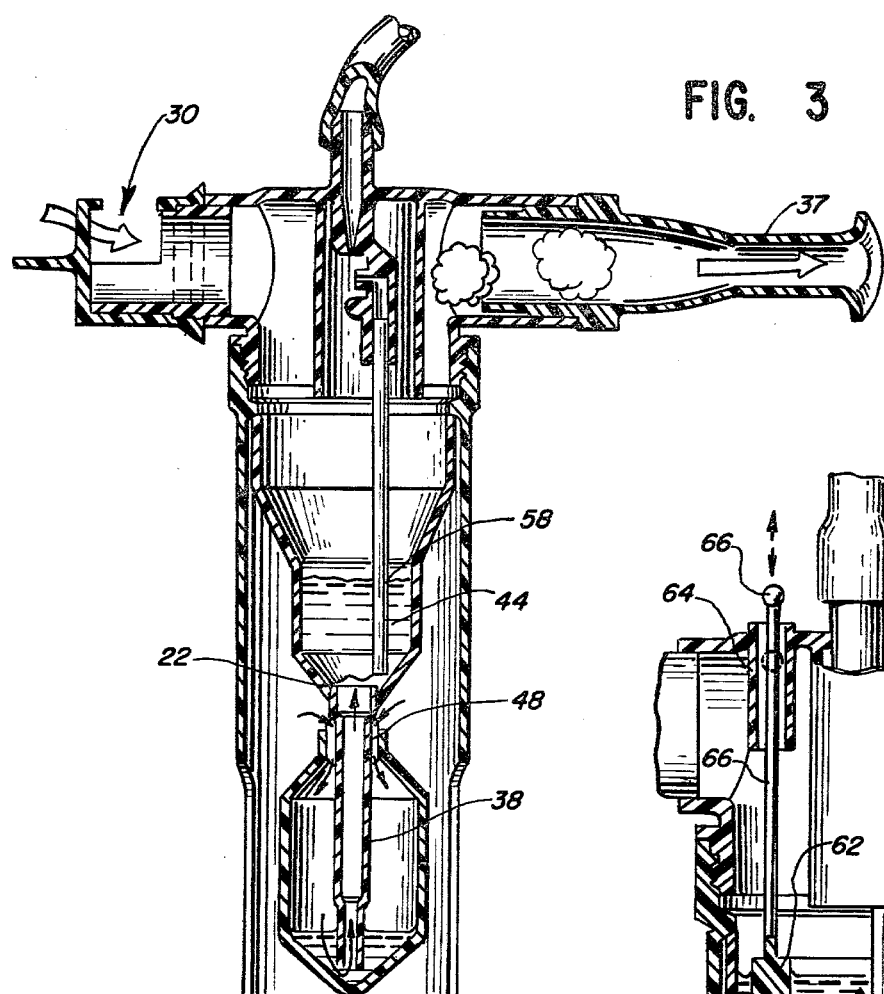
FIG. 3 is a vertical sectional view of the nebulizer of FIG. 1, shown in operation when the nebulizer is encountering a reduced pressure in the nebulizing chamber due to suction through the nebulized gas outlet.

Referring to FIGS. 1 through 3, a nebulizer 10 is shown which includes a housing wall which defines a nebulization chamber 12.

Oxygen inlet 14 communicates with oxygen line 16 at the exterior of the device, and includes an oxygen nozzle 18 for accelerating pressurized oxygen (in pure form or mixed with other gases as desired) to a velocity sufficient to permit aspiration of liquids by the Bernoulli effect.

A conventional liquid supply conduit 20 is provided which projects into a lower portion of nebulizing chamber 12 and defines an open lower end 22. Supply conduit 20 terminates in an aperture 24 which is positioned within the stream of oxygen defined by nozzle 18 for aspiration in the usual manner. Projection 26 serves as a target to help smash the liquid passing out of aperture 24 into myriads of nebulized droplets in a conventional manner.

Depending, open bottom tube 28 may be an integral part of the housing of nebulizer 10 and is shown to surround the liquid aspirating portions 18, 24, 26, all of which may be of generally conventional design, for example, of a design similar to the currently available nebulizer sold by Travenol Laboratories, Inc. of Deerfield, Illinois.

A conventional ambient air inlet port 30 is also provided, including an inner sleeve 32 defining an aperture 34 and surrounded by a rotatable cap 36 having aperture 35, so that the interaction of aperture 34 and aperture 35 provides an access port for ambient air of adjustable size, depending upon the rotational position of cap 36, the design of which may also be of generally conventional type.

In accordance with this invention, nebulizing chamber 12 defines a spike member 38 at its lower end which is adapted to penetrate an access port 40 of an ampule 42 which contains the liquid 44 to be nebulized as shown. In this present embodiment, spike 38 carries a plurality of longitudinal fins 46 at a position which generally is proximal to the nebulizing chamber 12. Fins 46 serve to provide vent passages 48 through the access port 40 of ampule 42.

Figure 4:
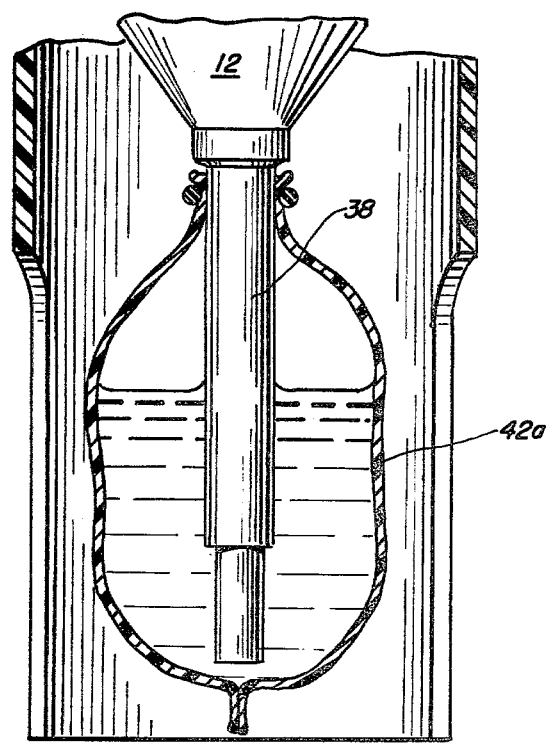
FIG. 4 is a fragmentary vertical sectional view of another embodiment of the nebulizer of this invention, similar except as shown to the nebulizer of FIG. 1.

Alternatively, as shown in FIG. 4, ampule 42a may comprise a flexible collapsible container such as a plastic bag. In this instance, no venting is required since the bag can simply expand and contract as liquid passes into and out of nebulizing chamber 12 by means of hollow spike 38.

Ampule 42 is shown to have a conical bottom 50, and is proportioned so that the apex of the conical bottom closely approximates the distal end 52 of spike 38, to permit a maximum amount of liquid contents of container 42 to be sucked upwardly by spike 38.

Depending sleeve 54 is carried by nebulizer 10 and extends downwardly to surround and protect the lower portion of nebulizing chamber 12, spike 38 and ampule 52. Sleeve 54 may carry longitudinally positioned slots 56 extending from the lower end of sleeve 54 upwardly a substantial distance, for example, about halfway to permit the user to reach inwardly of the sleeve 54 with the fingers to engage and disengage ampule 42. Preferably, a pair of diametrically opposed slots 56 are used in sleeve 54.

Nebulized gas outlet 37 is typically placed in a patient's mouth.

Accordingly, as the patient breathes in, the suction exerted through outlet 37 within nebulizing chamber 12 is controlled by adjustable air inlet port 30 to provide a variable opening to the exterior. If sufficient suction pressure for the specific opening size of port 30 is provided, a reduced pressure is created in nebulizing chamber 12 that causes liquid 44 to be sucked upwardly through spike 38 into nebulizing chamber 12 to create a liquid level 58 in chamber 12. With sufficient suction, the liquid level 58 flows over the position of lower end 22 of the liquid supply conduit 20 for the nebulizing means. When this happens, as oxygen is squirted through inlet 18, nebulization takes place with nebulized gas 60 passing out of outlet 37.

When the suction pressure through outlet 37 is terminated, the pressure within nebulizing chamber 12 quickly rises to ambient, with the result that the liquid 44 flows out of chamber 12 through spike 38 back into ampule 42. As soon as liquid level 58 falls below the level of open end 22, no further liquid supply for the nebulizing means is provided, so that the nebulization process terminates shortly thereafter.

As liquid passes into and out of ampule 42, air correspondingly passes into and out of vent passages 48.

As a result of this, the adjustment of valve 30 permits a wide range of suction pressures applied through outlet 37 which may trigger the nebulization by causing the liquid level in chamber 12 to rise above the level of open end 22 of the supply conduit 20. The distance from the lower end of spike 38 to open end 22 may preferably be about 2 to 5 cm. to provide a relatively low suction head necessary to initiate nebulization.

The device of this invention is of course highly versatile in its controllability of the selected minimum suction pressure necessary to permit nebulization. Accordingly, the device of this invention can be used as an incentive spirometer, while at the same time providing nebulization as desired to a patient for other purposes. The liquid level 58, particularly with respect to its relative position to open end 22 and volume indicia 60 can be used as an indicator of the vigor of breathing exhibited by the patient, with each individual breath being separately measurable.

Figure 5:
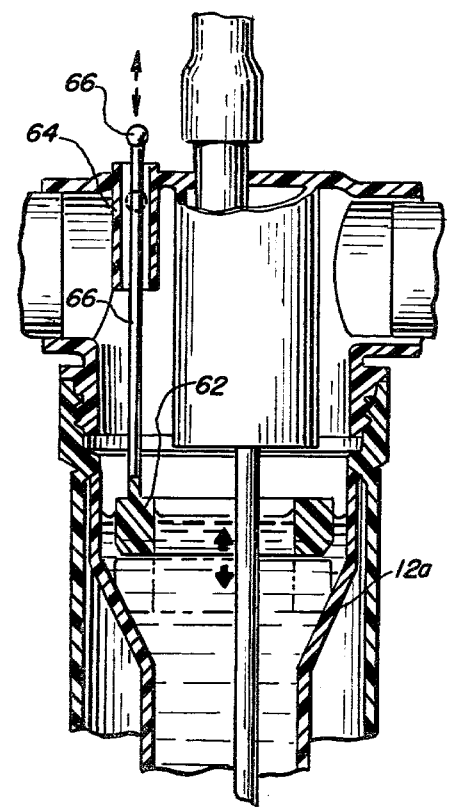
FIG. 5 is a fragmentary elevational view of another embodiment of the nebulizer of this invention, utilizing a float indicator member to show that adequate suction pressure is being achieved for nebulization.

In the alternative, FIG. 5 shows a device which is similar to the device of Claims 1 through 3 except as otherwise indicated. Specifically, an annular float member 62 is provided within nebulizing chamber 12a. Aperture member 64 comprising an elongated sleeve, open at the top of the nebulizer, is also provided. Upstanding member 66 is connected to the float member 62, and resides in part in the aperture member 64. Accordingly, liquid flows into nebulizing chamber 12 by suction. Float member 62 is elevated, causing upstanding indicating member 66 to project outwardly above aperture sleeve 64, which gives a visual indication of the fact that the liquid level 58 has reached the level of open end 22 of supply conduit 20. When the liquid level falls in chamber 12, upstanding indicator member 66 disappears into sleeve aperture 64.

Figure 6:
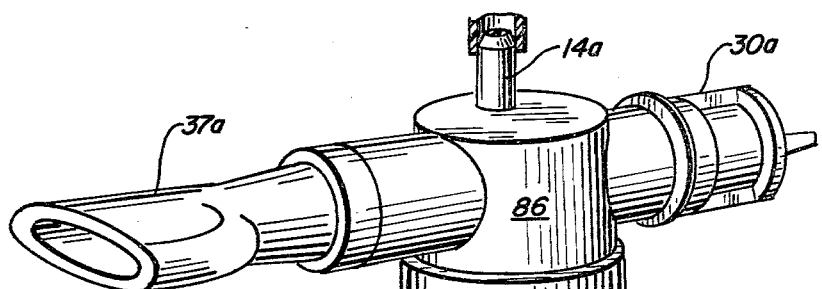
FIG. 6 is a perspective view of another embodiment of the nebulizer of this invention.
Figure 6:
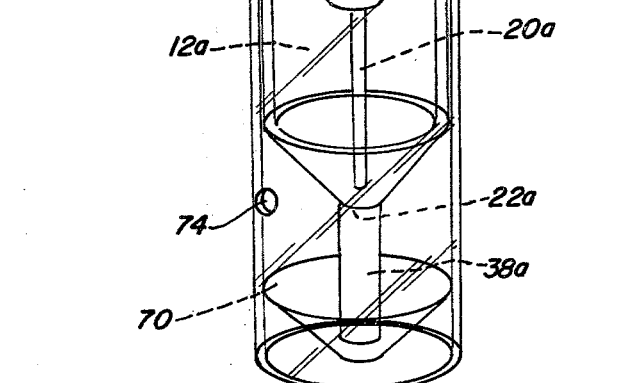

Referring to FIG. 6, another nebulizer in accordance with this invention is shown. Basically, the structure of the nebulizer is similar to the nebulizer of FIGS. 1 through 3 except as otherwise indicated, having a nebulized gas outlet 37a, an ambient air inlet port 30a, oxygen inlet 14a, and related parts similar to the previous embodiment.

Liquid supply conduit 20a projects from nebulizing chamber 12a to central chamber 71, which defines an open lower end 22a and a liquid suction conduit 38a, which in this embodiment is not necessarily a penetrating spike.

Conduit 38a extends downwardly into a vented chamber 70 defining a conical, closed bottom 72, which is an integral part of the nebulizer assembly. Chamber 70 is vented through an appropriate vent such as aperture hole 74, with the walls of chamber 70 defining, if desired, volume indicating scribe lines (FIG. 7) 76 as an indicator of the amount of liquid present in chamber 70.

The walls of chamber 70 are part of a lower tubular member 78 which may be attached in telescoping relation by gluing or a tight interference fit to an upper tubular member 80, which, in turn, defines nebulizing chamber 12a and depending tubular member 38a. Upper tubular member 80 defines at its upper end inner helical screw threads 82, which are adapted to mate with outer helical screw threads 84, defined on housing 86 which encloses the central, upper portion of the nebulizer including open bottom tube 28a. Tube 28a encloses the liquid aspirating portions of the nebulizer, which are of a design similar to the previous embodiments.

Accordingly, the upper and lower tubular member 78, 80 may be separated from housing 86, and the liquid for administration may be added to nebulization chamber 12a, from where it flows through tube 38a into the liquid storage chamber 70. Tubular members 78, 80 are then twisted into tight connection with housing 86, and the nebulizer is ready to function in a manner similar to that described with respect to the previous embodiments.

Conical partition 87 defines oversize aperture 89 to permit tube 20a to pass through with a clearance. Hence, condensed liquid in nebulization chamber 12a can fall back into chambers 71 and 70, while nebulized gases are generally confined above partition 87.

Figure 7:
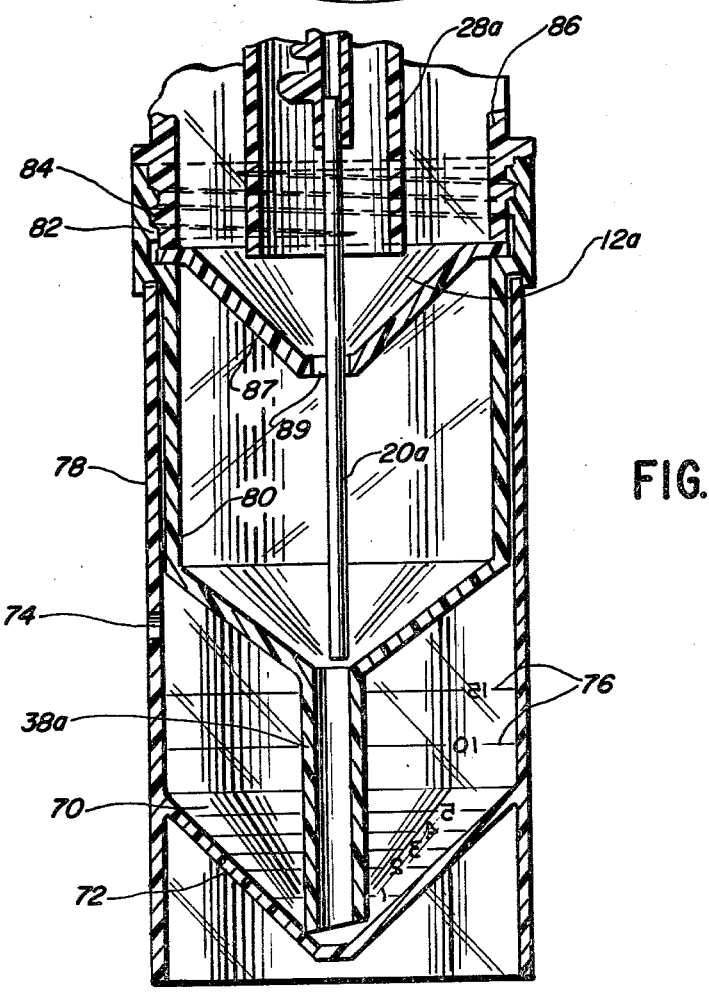
FIG. 7 is a fragmentary view taken in vertical section of the lower portion of the nebulizer of FIG. 6.

Referring to FIGS. 8 through 10, an embodiment of the nebulizer of this invention is shown similar to the embodiment of FIGS. 6 and 7, except for the structure of connection of the upper and lower tubular members. As in the previous embodiment, the nebulizer of FIGS. 8 through 10 carries a nebulized gas outlet 37b, an air inlet port 30b, and an upper housing 86b, which encloses the nebulizing components in a manner similar to the previous embodiments.

Lower tubular member 90 is attached by a slot and stud coupling structure to upper tubular member 92 which, in turn, is attached to lower skirt 94 of housing 86b.

Specifically, lower tubular member 90 defines a pair of diametrically opposed slots 96, 98 which have one end passing across the upper edge of tubular member 90, and adapted to engage with diametrically opposed studs 100 positioned on the upper tubular member 92. Thus, the two tubular members may be locked together by inserting each stud 100 into the angled slots 96, 98 and twisting to lock.

Correspondingly, upper tubular member 92 also defines a pair of slots 102, 104 which communicate across the upper edge of tubular member 92 and are adapted to mate with diametrically opposed studs 106 on lower skirt 94 of the upper housing 86b so that, correspondingly, the respective studs 106 may be inserted into slots 102, 104. Thus, the upper tubular member 92 can be locked into housing 86b with a twisting motion, for more rapid locking and removal of the respective tubular members 90, 92.

As in the previous embodiment, conical floor member 106 permits tube 20c, which functions in the manner of the previous embodiments, to pass through oversize aperture 108, leaving room for non-nebulized or condensed liquid to run downwardly through aperture 108 back into the liquid supply chamber 70b, which is similar in function to chamber 70 of the previous embodiment.

Vent hole 74b is provided for a purpose similar to that of the previous embodiment.

The above has been offered for illustrative purposes only and is not intended to limit the invention of this application, which is as defined in the claims below.

That which is claimed is:

1. In a nebulizer for forming a liquid mist in a stream of gas, which comprises a nebulizing chamber, a gas inlet communicating with said nebulizing chamber, a liquid supply conduit within said nebulizing chamber, means for nebulizing liquid from said supply conduit into gas entering said nebulizing chamber through said gas inlet, and an outlet for nebulized gas communicating with said nebulizing chamber, the improvement comprising, in combination:

a liquid suction conduit extending from and communicating with said nebulizing chamber, means for positioning a source of liquid below said nebulizing chamber and for communicating said source of liquid with said liquid suction conduit, said liquid supply conduit defining an open lower end within said nebulizing chamber below said nebulizing means, whereby the application of suction to said outlet can cause liquid to be drawn through said liquid suction conduit into said nebulizing chamber, to fill said chamber to the depth of said open lower end of the liquid supply conduit, to permit nebulization to occur, and upon the cessation of said suction, said liquid runs out of said nebulizing chamber through the liquid suction conduit, to reduce the level of liquid in the nebulizing chamber to expose said open lower end for terminating said nebulization.

2. The nebulizer of claim 1 in which adjustable atmospheric air vent means is provided in communication with the nebulizing chamber, whereby the amount of suction through said outlet which is necessary to permit nebulization to take place may be adjusted by appropriate adjustment of the aperture size of said air vent means.

3. The nebulizer of claim 2 in which said nebulizer defines a chamber about said liquid suction conduit permanently attached to said nebulizer chamber, said chamber includes means communicating the interior thereof to the atmosphere.

4. The nebulizer of claim 3 in which said chamber surrounding the liquid suction conduit defines a generally conical bottom, with the apex of said conical bottom being positioned adjacent the lower end of said liquid suction conduit.

5. The nebulizer of claim 4 in which said chamber which surrounds the liquid suction conduit defines a wall and wherein said communicating means comprises a vent hole therein.

6. The nebulizer of claim 5 in which said nebulizing chamber is defined by an upper tubular member and said chamber which surrounds said liquid suction conduit is defined by a lower tubular member, said upper tubular member carrying said lower tubular member and being removably attachable to the remainder of said nebulizer.

7. The nebulizer of claim 5 in which said lower tubular member connects with said upper tubular member by stud and slot means for removable attachment, and said upper tubular member connects with the remainder of the nebulizer with stud and slot means for removable attachment.

8. The nebulizer of claim 5 in which partition means surround said liquid supply conduit at a position between the ends thereof.

9. The nebulizer of claim 2 in which said liquid suction conduit is defined by a hollow spike member extending from the bottom of said nebulizing chamber, said source of liquid comprising an ampule which contains liquid for nebulization having an aperature in the top thereof, and further including means for venting said ampule to the atmosphere, said spike member passing through said aperture and terminating at the bottom of said ampule.

10. The nebulizer of claim 9 in which said means for venting the ampule comprise a plurality of longitudinally disposed fins positioned on a portion of said spike spaced from the lower end thereof and adapted to be positioned within the mouth of said ampule to define said venting means 11. The nebulizer of claim 10 in which said ampule defines a conical bottom adjacent the lower end of said spike member.

12. The nebulizer of claim 1 in which said liquid suction conduit is a hollow spike extending downwardly from the bottom of said nebulizing chamber, said source of liquid comprising a flexible collapsible container which contains liquid for nebulization having an access port therein, said spike passing through said access port of said flexible collapsible container and terminating adjacent the lower end of said container.

13. The nebulizer of claim 1 in which said nebulizing chamber contains a floating member, an aperture in the upper wall of said nebulizing chamber, and an elongated member occupying said aperture, whereby, upon the passage of liquid through said suction conduit into said nebulizing chamber, the floating member rises with the liquid level, causing said upstanding member to rise upwardly out of said aperture for a visual indication of the presence of liquid in said nebulizing chamber.

14. The nebulizer of claim 1 in which a depending sleeve encloses at least the lower portion of said nebulizing chamber and said liquid suction conduit, said liquid suction conduit includng means for detachably receiving a liquid containing ampule, said sleeve being proportioned to receive said liquid-containing ampule for use as said source of liquids.

15. The nebulizer of claim 14 in which said liquid-containing ampule is separable from said nebulizer, to be independently selected and installed on the spike at the time of use.

16. In a nebulizer for forming a liquid mist in a stream of gas, which comprises a nebulizing chamber, a gas inlet communicating with said nebulizing chamber, a liquid supply conduit within said nebulizing chamber, means for nebulizing liquid from said supply conduit into gas entering said nebulizing chamber through said gas inlet, and an outlet for nebulized gas communicating with said nebulizing chamber, the improvement comprising, in combination:

a liquid suction conduit extending from and communicating with said nebulizing chamber, means for positioning a source of liquid below said nebulizing chamber, and for communicating said source of liquid with said liquid suction conduit said liquid supply conduit defining an open lower end within said nebulizing chamber below said nebulizing means; ampule means, communicating with said liquid suction conduit and containing a supply of liquid, whereby the application of suction to said outlet then causes liquid to be drawn through said liquid suction conduit into said nebulizing chamber, to fill said chamber to the depth of said open lower end of the liquid supply conduit, to permit nebulization to occur, and upon the cessation of said suction, said liquid runs out of said nebulizing chamber through the liquid suction conduit back into said ampule means, to reduce the level of liquid in the nebulizing chamber to expose said lower end for terminating said nebulization.

17. The nebulizer of claim 16 in which said ampule means is attached to said liquid suction conduit with an aseptic, permanent seal.

* * * * *